United States Patent
Lin et al.

(10) Patent No.: US 12,383,717 B2
(45) Date of Patent: Aug. 12, 2025

(54) MEDICINE POWDER DELIVERY DEVICE AND MEDICINE BOTTLE THEREOF AND BOTTLE CAP OF MEDICINE BOTTLE

(71) Applicant: ENDO-PEACE MEDICAL, Tainan (TW)

(72) Inventors: Xi-Zhang Lin, Tainan (TW); Chih-Hong Chen, Tainan (TW); Chuan-Pin Lin, Kaohsiung (TW); Ying-Chen Chen, Tainan (TW)

(73) Assignee: ENDO-PEACE MEDICAL, Tainan (TW)

( * ) Notice: Subject to any disclaimer, the term of this patent is extended or adjusted under 35 U.S.C. 154(b) by 885 days.

(21) Appl. No.: 17/444,235

(22) Filed: Aug. 2, 2021

(65) Prior Publication Data

US 2023/0031601 A1   Feb. 2, 2023

(51) Int. Cl.
*A61M 35/00* (2006.01)
*A61J 1/00* (2023.01)
*B05B 7/14* (2006.01)

(52) U.S. Cl.
CPC ........... *A61M 35/00* (2013.01); *B05B 7/1404* (2013.01); *B05B 7/1486* (2013.01); *A61J 1/00* (2013.01); *A61M 2202/064* (2013.01); *A61M 2205/071* (2013.01)

(58) Field of Classification Search
CPC ............ A61M 35/00; A61M 2202/064; A61M 2205/071; A61M 5/178; A61M 25/0045; A61M 39/24; B05B 7/1404; B05B 7/1486; B05B 11/062; A61J 1/00
See application file for complete search history.

(56) References Cited

U.S. PATENT DOCUMENTS

| | | | | |
|---|---|---|---|---|
| 2,738,234 A | * | 3/1956 | Anderson | B23K 7/08 406/75 |
| 5,634,900 A | * | 6/1997 | Makino | A61M 15/0065 128/203.15 |
| 5,875,776 A | * | 3/1999 | Vaghefi | A61M 15/02 128/203.15 |

(Continued)

FOREIGN PATENT DOCUMENTS

| | | | | |
|---|---|---|---|---|
| CN | 105963853 A | * | 9/2016 | A61M 35/00 |
| CN | 107311100 A | * | 11/2017 | B67D 7/02 |

(Continued)

*Primary Examiner* — Rebecca E Eisenberg
*Assistant Examiner* — Matthew Wrubleski
(74) *Attorney, Agent, or Firm* — Rosenberg, Klein & Lee

(57) ABSTRACT

A medicine powder delivery device and a medicine bottle thereof and a bottle cap of the medicine bottle are disclosed. The medicine powder delivery device includes a medicine bottle and a gas supply member. The medicine bottle has a bottle body and a bottle cap. The bottle body is filled with a medicine powder. When the bottle body is inverted, the bottle body has an unfilled space that is not filled with the medicine powder. The bottle cap includes a cap body, a medicine delivery tube, and a gas delivery tube. The cap body covers the bottle body. The medicine delivery tube and the gas delivery tube extends into the cap body. The medicine delivery tube communicating with the bottle body the gas delivery tube inserted into the unfilled space of the bottle body. The gas supply member is connected to the gas delivery tube.

10 Claims, 9 Drawing Sheets

(56) References Cited

U.S. PATENT DOCUMENTS

| 10,993,877 | B2* | 5/2021 | Sealfon | A61M 5/3298 |
| 2013/0211320 | A1* | 8/2013 | Alkhamesi | A61M 13/00 |
| | | | | 604/24 |
| 2020/0101476 | A1* | 4/2020 | Pic | A61M 11/02 |

FOREIGN PATENT DOCUMENTS

| TW | M617868 U | 10/2021 |
| TW | I824255 B | 12/2023 |

* cited by examiner

MEDICINE POWDER DELIVERY DEVICE AND MEDICINE BOTTLE THEREOF AND BOTTLE CAP OF MEDICINE BOTTLE

FIELD OF THE INVENTION

The present invention relates to a medicine powder delivery device and a medicine bottle thereof and a bottle cap of the medicine bottle, and more particularly to a medicine bottle provided with an external gas supply member to input a gas to an unfilled space of the medicine bottle instead of compressing the medicine bottle, so that the medicine powder in the medicine bottle can be output under pressure.

BACKGROUND OF THE INVENTION

There are various medicine applicators on the market.

As shown in FIG. 7 through FIG. 9, a conventional press-type medicine applicator A includes a compressible medicine storage bottle A1 and a nozzle A2. The nozzle A2 is in communication with the compressible medicine storage bottle A1. The compressible medicine storage bottle A1 has a plurality of neck portions A11 arranged at intervals. When in use, the compressible medicine storage bottle A1 is pressed for the powder B in the compressible medicine storage bottle A1 to be sprayed toward the wound through the nozzle A2 under pressure.

When the compressible medicine storage bottle A1 is pressed, the powder B may be accumulated at the neck portions A11, making it difficult to press the compressible medicine storage bottle A1. The powder B in the compressible medicine storage bottle A1 receives insufficient pressure, so the force sprayed from the nozzle A2 is small and uneven.

SUMMARY OF THE INVENTION

In view of the defects of the prior art, the primary object of the present invention is to provide a medicine powder delivery device and a medicine bottle thereof and a bottle cap of the medicine bottle. The medicine powder delivery device comprises a medicine bottle and a gas supply member.

The medicine bottle has a bottle body and a bottle cap. The bottle body has a bottle mouth. The bottle body is filled with a medicine powder. When the bottle body is inverted, the bottle body has an unfilled space that is not filled with the medicine powder. The bottle cap includes a cap body, a medicine delivery tube, and a gas delivery tube. The cap body has a top portion and a cover portion opposite to the top portion. The cap body covers the bottle body to close the bottle mouth. The medicine delivery tube extends from the top portion into the cap body. The medicine delivery tube has a medicine feeding end passing through the top portion and communicating with the bottle mouth. The gas delivery tube extends from the top portion into the cap body. The gas delivery tube has a gas feeding end passing through the top portion and extending out of the cover portion to be inserted into the bottle body from the bottle mouth. The gas feeding end extends into the unfilled space.

The gas supply member is connected to the gas delivery tube. When in use, a gas is input from the gas supply member to the unfilled space of the medicine bottle, so that the medicine powder is under pressure to be output from the medicine delivery tube.

Preferably, the gas supply member includes a gas-pumping member and a check valve. The check valve is connected between the gas delivery tube and the gas-pumping member. Preferably, the gas supply member further includes a powder filter. The powder filter is connected between the gas delivery tube and the check valve. The check valve includes a first check portion and a second check portion. The first check portion is connected to the powder filter. The second check portion communicates with an outside and is located between the first check portion and the gas-pumping member.

Preferably, the medicine powder delivery device further comprises a catheter connected to the medicine delivery tube.

Preferably, the medicine powder delivery device further comprises dustproof sleeves sleeved on respective ends of the medicine delivery tube and the gas delivery tube, located on the top portion of the cap body.

Through the above technical features, the following effects can be achieved:

1. In the present invention, the medicine bottle is not compressed, and the external gas supply member is used to input a gas into the unfilled space of the medicine bottle, so that the medicine powder in the medicine bottle can be output under pressure. There will be no problem that the medicine powder is jammed in the medicine bottle to affect the compression of the medicine bottle.

2. In the present invention, the gas supply member is provided with the powder filter, which can prevent the powder from entering the gas-pumping member when the gas-pumping member is repeatedly pumped.

3. When not in use, the dustproof sleeves are sleeved on the ends of the medicine delivery tube and the gas delivery tube, respectively. Thus, the medicine delivery tube and the gas delivery tube won't be contaminated with dust, dirt or germs, and the medicine powder in the medicine bottle won't be contaminated.

DESCRIPTION OF THE PREFERRED EMBODIMENTS

Embodiments of the present invention will now be described, by way of example only, with reference to the accompanying drawings.

Figure 1:
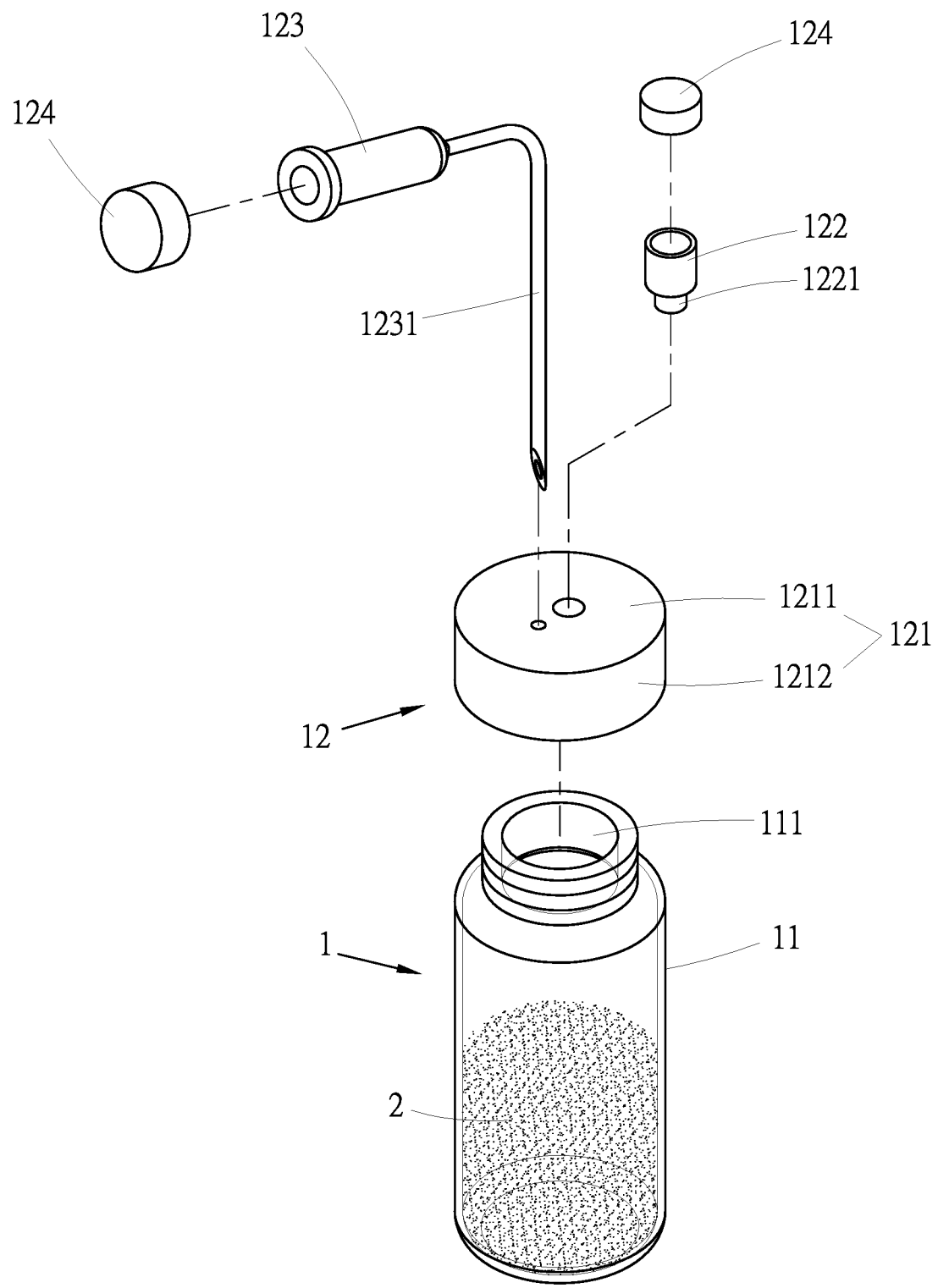
FIG. 1 is an exploded view of the medicine bottle according to an embodiment of the present invention.
Figure 2:
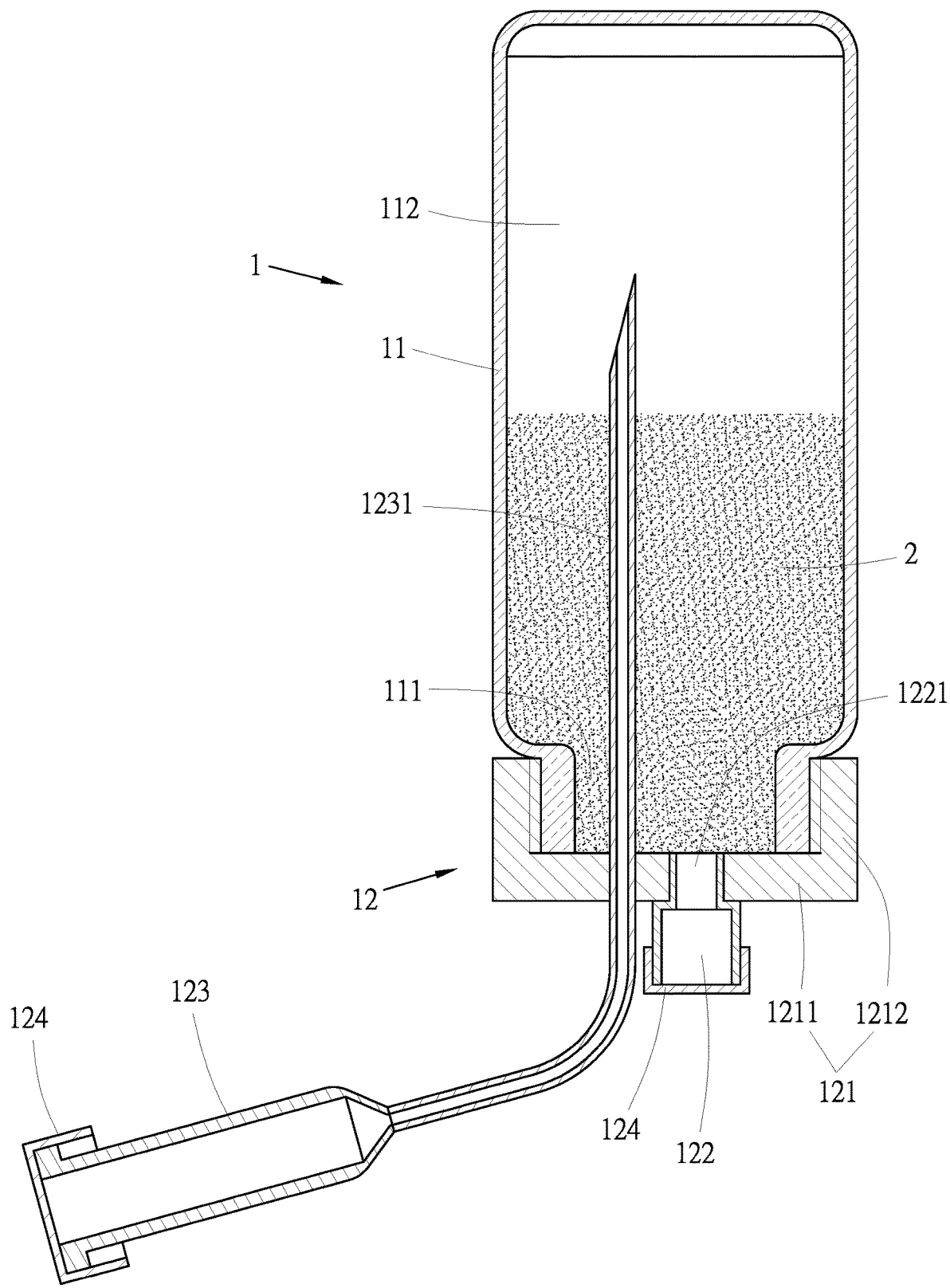
FIG. 2 is an assembled cross-sectional view of the medicine bottle according to the embodiment of the present invention in an upside-down state.

Referring to FIG. 1 and FIG. 2, a medicine bottle 1 according to an embodiment of the present invention comprises a bottle body 11 and a bottle cap 12. The bottle body 11 has a bottle mouth 111. The bottle body 11 is filled with a medicine powder 2. The bottle cap 12 includes a cap body 121, a medicine delivery tube 122, a gas delivery tube 123, and two dustproof sleeves 124. The cap body 121 has a top portion 1211 and a cover portion 1212 opposite to the top portion 1211. The cap body 121 covers the bottle body 11 to close the bottle mouth 111. The medicine delivery tube 122 extends from the top portion 1211 into the cap body 121. The medicine delivery tube 122 has a medicine feeding end 1221 passing through the top portion 1211 and communicating with the bottle mouth 111. For example, the medicine feeding end 1221 is flush with the underside of the top portion 1211. The gas delivery tube 123 extends from the top portion 1211 into the cap body 121. The gas delivery tube 123 has a gas feeding end 1231 passing through the top portion 1211 and extending out of the cover portion 1212 to be inserted into the bottle body 11 from the bottle mouth 111. When the medicine bottle 1 is inverted, the gas feeding end 1231 extends into an unfilled space 112 of the bottle body 11 where the medicine powder 22 is not filled. The dustproof sleeves 124 are respectively sleeved on the ends of the medicine delivery tube 122 and the gas delivery tube 123, located on the top portion 1211 of the cap body 121. Thus, when the medicine bottle 1 is not in use, the medicine delivery tube 122 and the gas delivery tube 123 won't be contaminated with dust, dirt or germs, and the medicine powder 2 in the medicine bottle 1 won't be contaminated.

Figure 3:
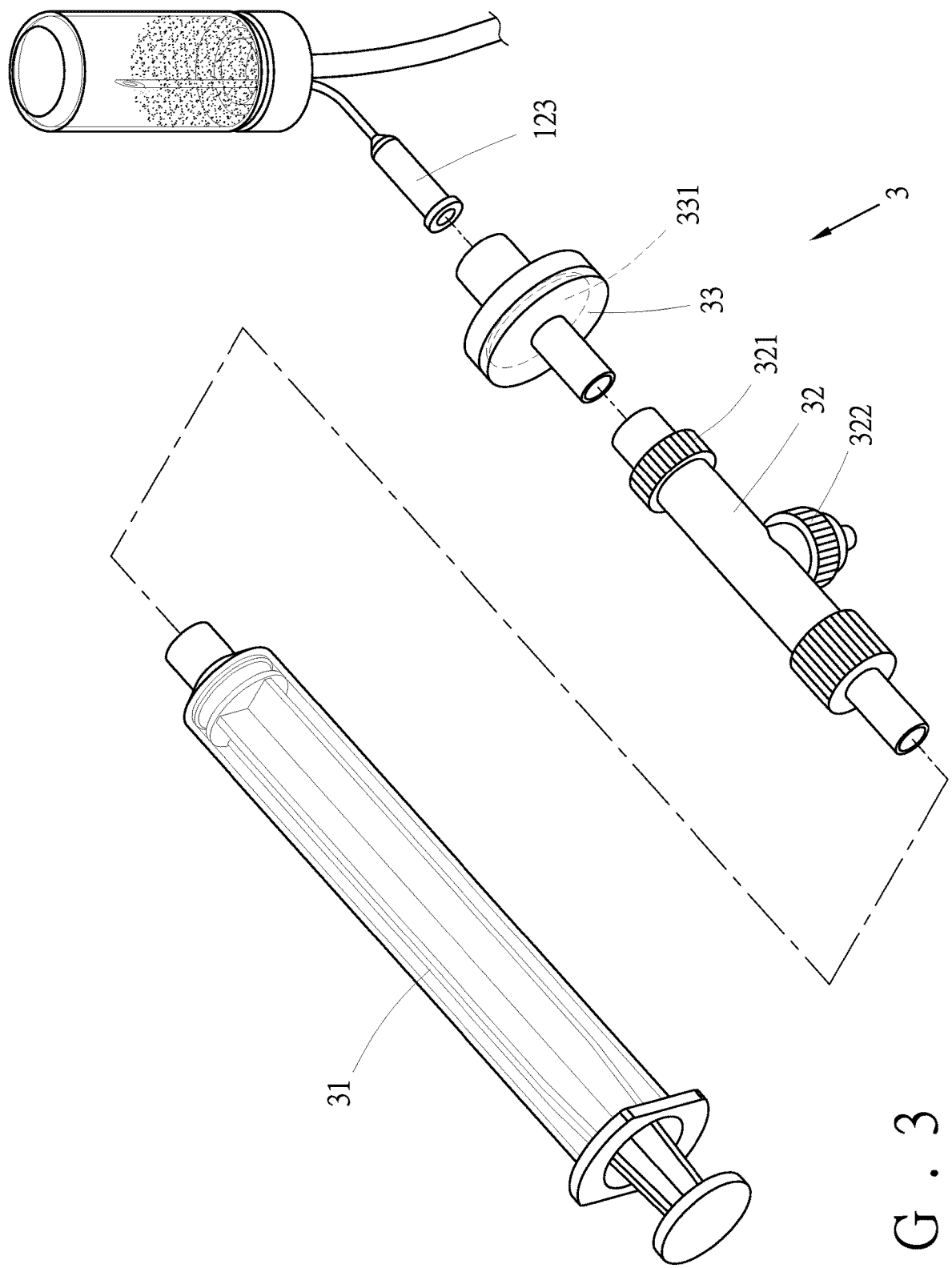
FIG. 3 is an exploded view of the medicine powder delivery device according to the embodiment of the present invention.
Figure 4:
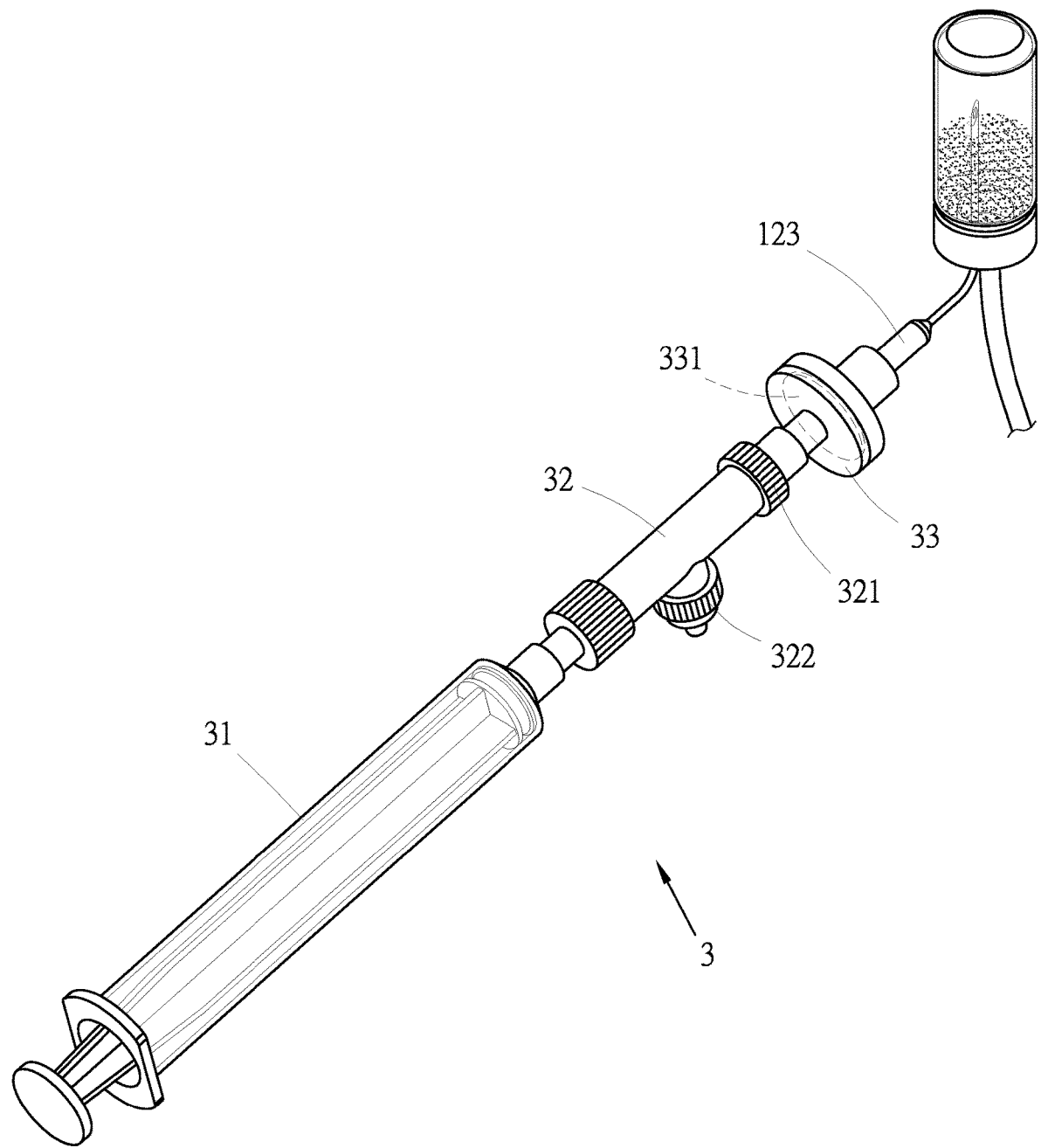
FIG. 4 is an assembled perspective view of the medicine powder delivery device according to the embodiment of the present invention.

Referring to FIG. 3 and FIG. 4, a medicine powder delivery device according to an embodiment of the present invention comprises a gas supply member 3. The gas supply member 3 is connected to the gas delivery tube 123. In this embodiment, the gas supply member 3 includes a gas-pumping member 31, a check valve 32, and a powder filter 33. The powder filter 33 is coupled to the gas delivery tube 123. A filtering plate 331 is provided in the powder filter 33. The check valve 32 is coupled to the powder filter 33. The gas-pumping member 31 is coupled to the check valve 32. In this embodiment, the gas-pumping member 31 is a syringe. The check valve 32 includes a first check portion 321 and a second check portion 322. The first check portion 321 is connected to the powder filter 33. The second check portion 322 communicates with the outside and is located between the first check portion 321 and the gas-pumping member 31.

Figure 5:
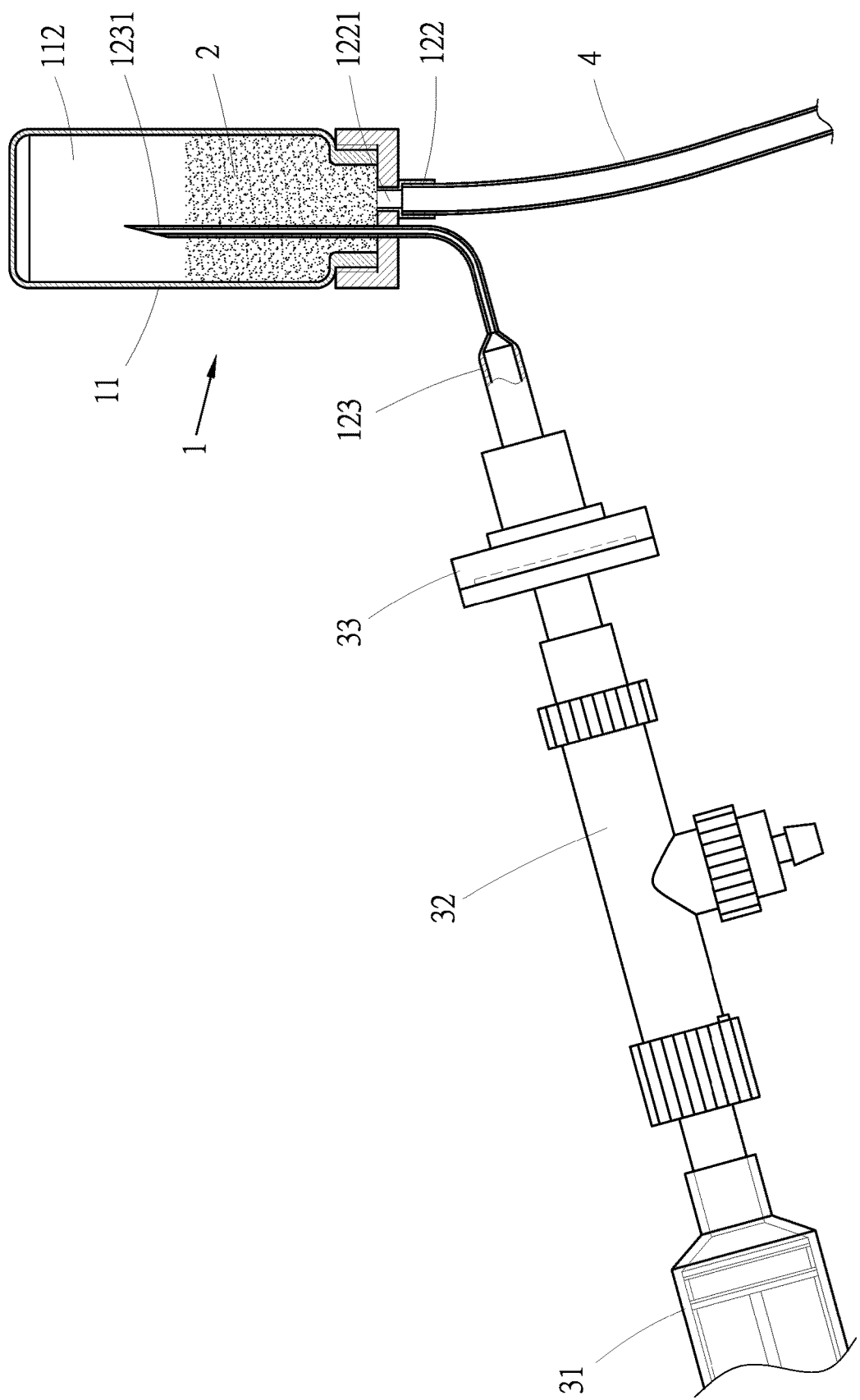
FIG. 5 is a schematic view of the medicine powder delivery device according to the embodiment of the present invention when in use.

Referring to FIG. 5, when used for intra-cavity medicine delivery, the medicine delivery tube 122 is connected with a catheter 4. The catheter 4 is inserted into the human body cavity and aimed at the place where the medicine is to be administered. After that, the gas-pumping member 31 pumps the gas into the unfilled space 112 of the bottle body 11 of the medicine bottle 1 through the gas feeding end 1231 of the gas delivery tube 123, so that the pressure of the unfilled space 112 is increased. At this time, the medicine powder 2 in the bottle body 11 will be squeezed by high pressure to enter the catheter 4 through the medicine delivery tube 122 from the medicine feeding end 1221. Then, the medicine is to be administered. In order to enable the medicine powder 2 to adhere to the place where the medicine is to be administered, the medicine powder 2 usually has the characteristic of being prone to coagulation after contact with blood, so the inner wall of the catheter 4 is coated with lipophilic substances to avoid the medicine powder 2 condensation and blockage in the catheter 4. The medicine feeding end 1221 is flush with the underside of the top portion 1211 to ensure that the medicine powder 2 in the bottle body 11 can be used up without remaining.

It should be further explained that since the medicine bottle 1 is not compressed, and the external gas supply member 3 is used to input a gas into the unfilled space 112 of the medicine bottle 1, so that the medicine powder 2 in the medicine bottle 1 can be output under pressure. Therefore, there will be no problem that the medicine powder is jammed in the medicine bottle to affect the compression of the medicine bottle as the prior art. The gas-pumping member 31 uses a syringe to pump the gas. Therefore, through the powder filter 33 and the check valve 32, the medicine powder 2 won't enter the gas-pumping member 31 because of negative pressure.

Figure 6:
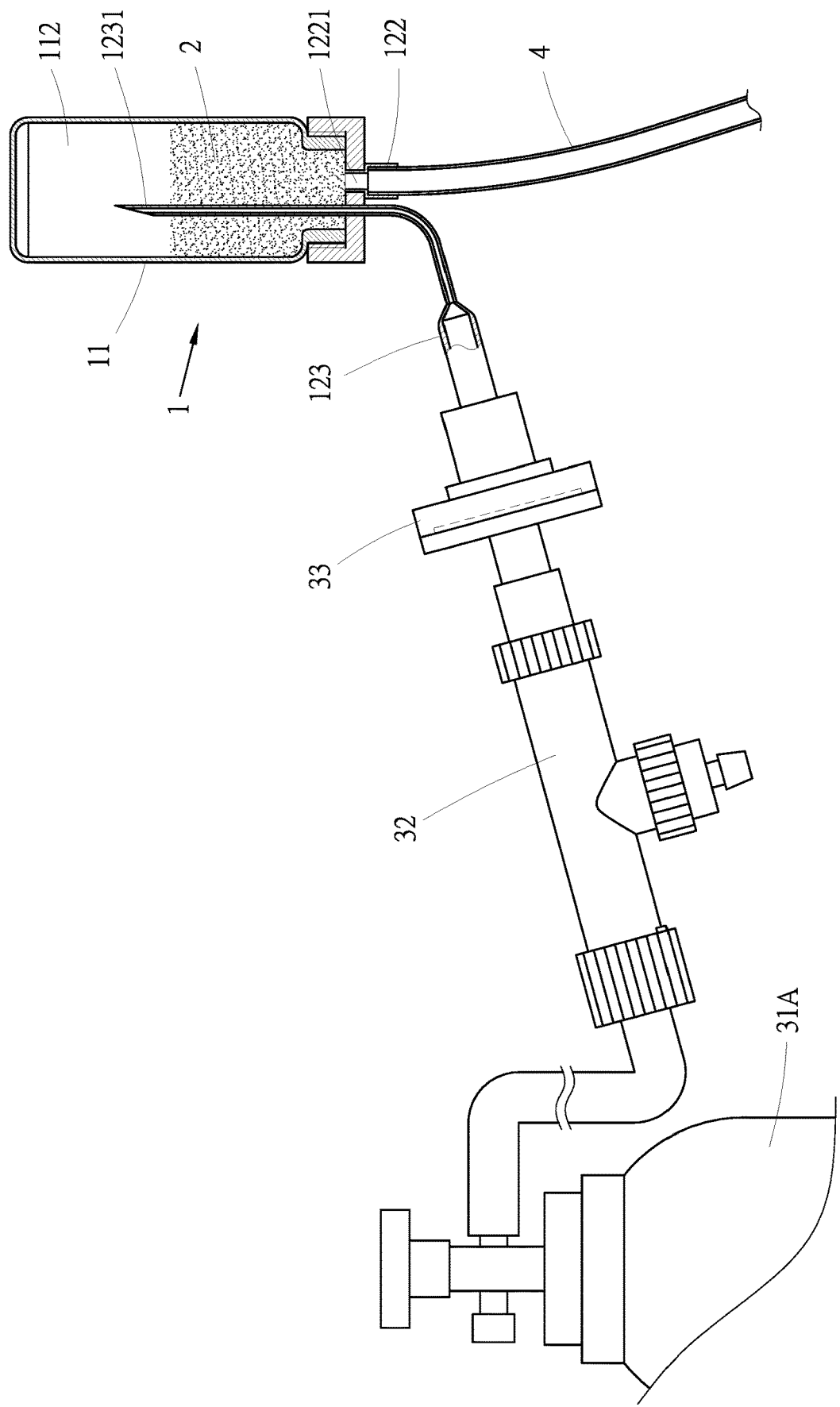
FIG. 6 is a schematic view of the medicine powder delivery device according to an alternative embodiment of the present invention when in use, wherein the gas-pumping member is a gas cylinder.
Figure 7:
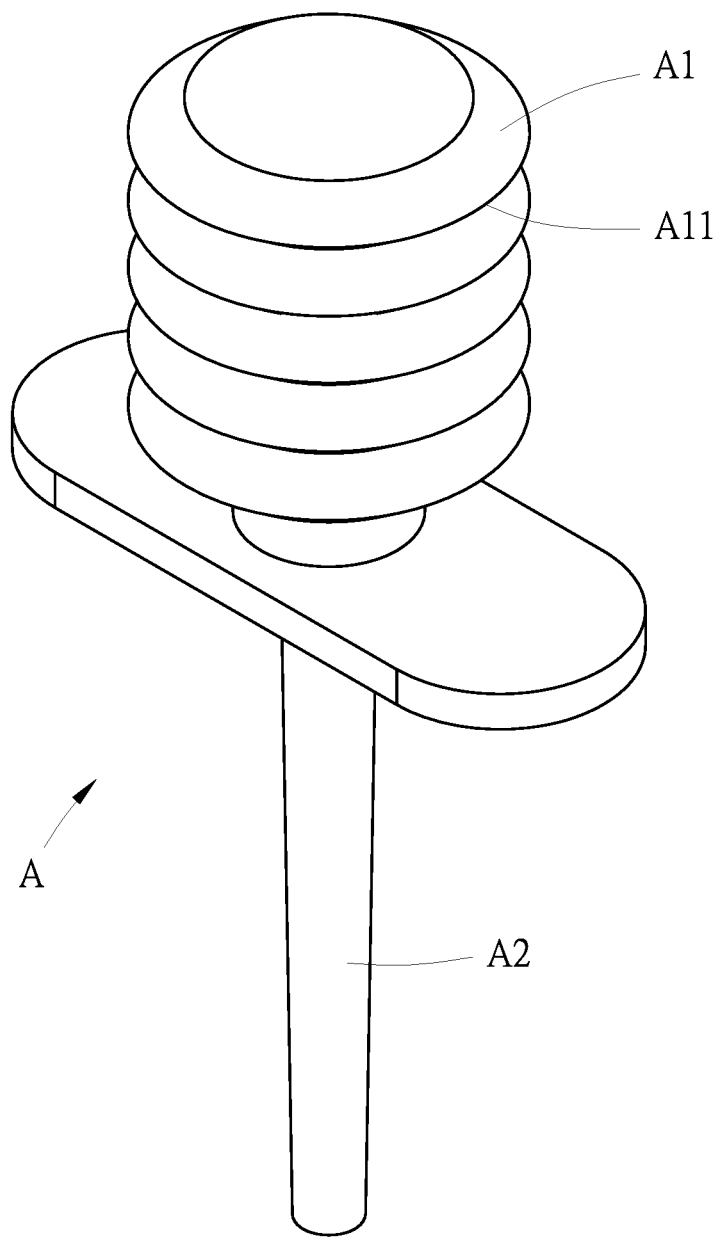
FIG. 7 is a perspective view of a conventional press-type medicine applicator.
Figure 8:
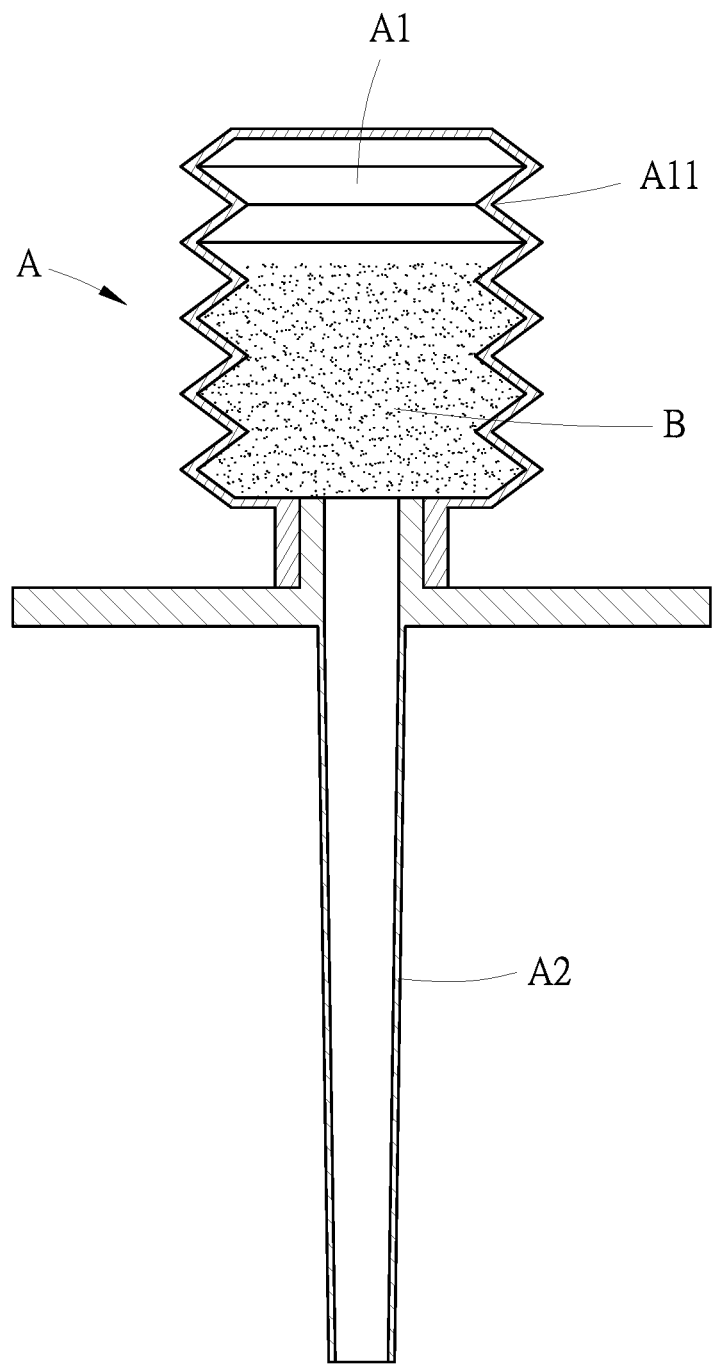
FIG. 8 is a cross-sectional view of the conventional press-type medicine applicator.
Figure 9:
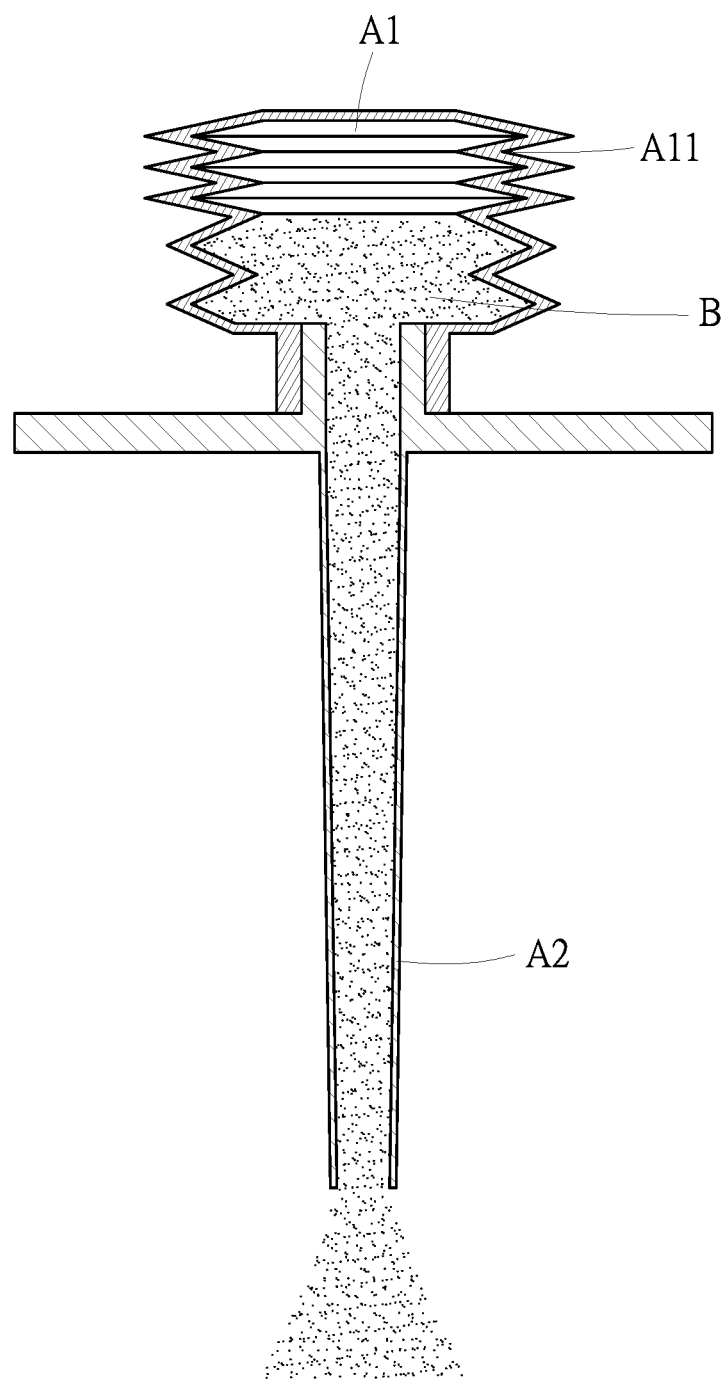
FIG. 9 is a schematic view showing the operation of the conventional press-type medicine applicator.

It is worth mentioning that the syringe is manually operated by medical personnel to pump the gas. However, according to an alternative embodiment of the present invention, the gas supply member 3 uses an automatic gas-pumping member 31A such as a gas cylinder (as shown in FIG. 6), in replacement of the syringe, to pump the gas automatically.

Although particular embodiments of the present invention have been described in detail for purposes of illustration, various modifications and enhancements may be made without departing from the spirit and scope of the present invention. Accordingly, the present invention is not to be limited except as by the appended claims.

What is claimed is:

1. A bottle cap for covering a bottle body of a medicine bottle, comprising:
    a cap body having a top portion and a cover portion extending from the top portion towards the bottle body of the medicine bottle;
    a medicine delivery tube extending from the top portion into the cap body and having a medicine feeding end passing through the top portion, the medicine feeding end being flush with an inner surface of the top portion of the cap body; and
    a gas delivery tube extending from the top portion into the cap body and having a gas feeding end passing through the top portion and extending out of the cover portion, the gas feeding end forming a continuous gas passage and having a length greater than a length of the medicine feeding end,
    wherein the medicine delivery tube and the gas delivery tube are separate and independent from each other, and wherein only the gas delivery tube extends into the bottle body of the medicine bottle.

2. The bottle cap as claimed in claim 1, further comprising dustproof sleeves sleeved on respective ends of the medicine delivery tube and the gas delivery tube.

3. A medicine bottle, comprising:
    a bottle body having a bottle mouth; and
    a bottle cap, the bottle cap including:
        a cap body having a top portion and a cover portion extending from the top portion towards the bottle body, the cap body covering the bottle mouth to thereby close the bottle body,
        a medicine delivery tube extending from the top portion into the cap body and having a medicine feeding end passing through the top portion and communicating with the bottle mouth, the medicine feeding end being flush with an inner surface of the top portion of the cap body, and
        a gas delivery tube extending from the top portion into the cap body and having a gas feeding end passing through the top portion and extending out of the cover portion for insertion into the bottle body, the gas feeding end forming a continuous gas passage and having a length greater than a length of the medicine feeding end, wherein the medicine delivery tube and the gas delivery tube are separate and independent from each other, and wherein only the gas delivery tube extends into the bottle body of the medicine bottle.

4. The medicine bottle as claimed in claim 3, further comprising dustproof sleeves sleeved on respective ends of the medicine delivery tube and the gas delivery tube.

5. A medicine powder delivery device, comprising:
a medicine bottle including a bottle body and a bottle cap, the bottle body having a bottle mouth, the bottle body being filled with a medicine powder, wherein when the bottle body is inverted, the bottle body has an unfilled space that is not filled with the medicine powder, the bottle cap including:
   a cap body having a top portion and a cover portion extending from the top portion towards the bottle body, the cap body covering the bottle mouth to thereby close the bottle body,
   a medicine delivery tube extending from the top portion into the cap body and having a medicine feeding end passing through the top portion and communicating with the bottle mouth, the medicine feeding end being flush with an inner surface of the top portion of the cap body, and
   a gas delivery tube extending from the top portion into the cap body and having a gas feeding end passing through the top portion and extending out of the cover portion for insertion into the bottle body, the gas feeding end forming a continuous gas passage and having a length greater than a length of the medicine feeding end, the gas feeding end thereby extending into the unfilled space, wherein the medicine delivery tube and the gas delivery tube are separate and independent from each other, and wherein only the gas delivery tube extends into the bottle body of the medicine bottle; and
a gas supply member connected to the gas delivery tube, wherein when the gas supply member is actuated, gas is input from the gas supply member to the unfilled space of the medicine bottle, the medicine powder being thereby pressurized for being output from the medicine delivery tube.

6. The medicine powder delivery device as claimed in claim 5, wherein the gas supply member includes a gas-pumping member and a check valve, and the check valve is connected between the gas delivery tube and the gas-pumping member.

7. The medicine powder delivery device as claimed in claim 6, wherein the gas supply member further includes a powder filter, and the powder filter is connected between the gas delivery tube and the check valve.

8. The medicine powder delivery device as claimed in claim 7, wherein the check valve includes a first check portion and a second check portion, the first check portion is connected to the powder filter, and the second check portion communicates with an outside and is located between the first check portion and the gas-pumping member.

9. The medicine powder delivery device as claimed in claim 5, further comprising a catheter connected to the medicine delivery tube.

10. The medicine powder delivery device as claimed in claim 5, further comprising dustproof sleeves sleeved on respective ends of the medicine delivery tube and the gas delivery tube.

* * * * *